United States Patent [19]

Miura et al.

[11] Patent Number: 5,621,165
[45] Date of Patent: Apr. 15, 1997

[54] VISCOSITY DETECTOR HAVING A NODE ALIGNMENT MECHANISM

[75] Inventors: Shinsuke Miura, Hachiohji; Norihiko Kumagai; Kenji Muraoka, both of Tokyo; Takashi Yoshimura, Kawasaki, all of Japan

[73] Assignee: Yamaichi Electronics Co., Ltd., Tokyo, Japan

[21] Appl. No.: 528,151

[22] Filed: Sep. 14, 1995

[30] Foreign Application Priority Data

Sep. 16, 1994 [JP] Japan .................................. 6-248432

[51] Int. Cl.⁶ ............................................. G01N 11/10
[52] U.S. Cl. ........................................ 73/54.27; 73/54.24
[58] Field of Search .............................. 73/54.24, 54.25, 73/54.26, 54.27, 54.28, 54.33, 54.32, 54.31, 54.34, 54.35, 54.38, 54.41

[56] References Cited

U.S. PATENT DOCUMENTS 4,566,181   1/1986   Matusik et al. ................ 73/54.25 X
4,811,593   3/1989   Miura et al. ..................... 73/54.26

OTHER PUBLICATIONS

Wazer et al., "Viscosity and Flow Measurement: A Laboratory Handbook of Rheology", Interscience Publishers, New York, pp. 373–376, QC 189 V3.

*Primary Examiner*—Michael Brock
*Attorney, Agent, or Firm*—Wenderoth, Lind & Ponack

[57] ABSTRACT

A vibrating member, including a vibration transmission shaft, is adapted to vibrate a liquid viscosity detector with respect to an axis of the shaft. The liquid viscosity detector is disposed at one end of the vibration transmission shaft so it can be dipped in a liquid to be measured. A bearing portion is disposed at an intermediate position of the vibration transmission shaft. The viscosity detector includes an inertia mass disposed on the vibration transmission shaft along the central axis thereof. The viscosity detector is positioned on the opposite side of the shaft relative to the liquid detector, with the bearing portion located therebetween. Also provided is a node alignment mechanism for displacing the whole inertia mass along the central axis of the shaft, or a part of the inertia mass toward or away from the shaft axis or along the direction of the axis.

5 Claims, 4 Drawing Sheets

[5,621,165]

VISCOSITY DETECTOR HAVING A NODE ALIGNMENT MECHANISM

BACKGROUND OF THE INVENTION

1. Field of the Invention

The present invention relates to a viscosity detector including a liquid detector provided at the end of a vibration transmission shaft.

2. Brief Description of the Prior Art

The inventors of the present invention has already proposed a viscosity detector having a liquid detector disposed at the end part of a vibration transmission shaft. The liquid detector is vibrated in a same direction in a liquid by driving the vibrating shaft about an axis line with a piezoelectric type vibrator to sense viscous resistance. The viscosity of the liquid is detected based on a variation of the vibration due to the viscous resistance as disclosed in U.S. Pat. No. 4,811,593 and U.S. Pat. No. 5,228,331.

Since the viscosity detector of the aforementioned type employs a system which vibrates the vibration transmission shaft and the liquid detector about an axis line at a resonance frequency by a vibrator which is adapted to vibrate in a circular direction, the vibrating shaft is supported in the vicinity of a node of the resonance, and the detector is correctly vibrated by fitting the vibration shaft to a housing of the viscosity detector or a container of a liquid to be measured.

However, the conventional viscosity detector has a problem in that the node of the resonance can be dislocated from the intended position due to a fabrication error, or an assembling error of the vibration transmission shaft, with the bearing portion and the liquid detector. The errors will cause the node of the resonance to be incoincident with the bearing portion, resulting in extremely degraded performance of the viscosity detector.

This problem also results in a viscosity detector which will not necessarily maintain the reliability of the design during construction or while in use.

SUMMARY OF THE INVENTION

The present invention has been developed in consideration of the aforementioned problems.

An object of the present invention is to provide a viscosity detector which is entirely free from the problems with the conventional viscosity detectors.

Other objects of the present invention are to provide a viscosity detector which assures that the viscosity of a liquid to be measured is exactly measured by positionally coinciding a node of the vibration transmission shaft with the bearing portion.

According to one aspect of the present invention, there is provided a viscosity detector including a vibration transmission shaft adapted to be vibrated by a vibrating member with respect to an axis line of the shaft. A liquid detector is disposed at one end of the vibration transmission shaft for being dipped in a liquid to be measured, and a bearing portion is disposed at the intermediate position of the vibration transmission shaft. The viscosity detector is characterized in that the viscosity detector includes an inertia mass disposed integrally on the vibration transmission shaft along the central axis and on the opposite side of the shaft relative to the liquid detector. A bearing portion is located between the liquid detector and the vibrating member. The apparatus also includes a node alignment mechanism for displacing the whole of the inertial mass along the central axis, or a part of the inertia mass in a direction toward or away from the central axis.

According to another aspect of the present invention, there is provided a viscosity detector including a vibration transmission shaft adapted to vibrate by a vibrating member about a central axis of the vibration transmission shaft. A liquid detector is disposed at one end of the vibration transmission shaft for being dipped in a liquid to be measured. A bearing portion is disposed at an intermediate position of the vibration shaft. The viscosity detector is characterized in that the viscosity detector includes an inertia mass disposed integrally on the vibration shaft along the central axis and is located on the opposite side of the shaft relative to the liquid detector. Moreover, the apparatus includes a node alignment mechanism for displacing the whole or a part of the inertia mass in the direction along the central axis.

With the viscosity detector constructed in the above described manner, the vibration of the liquid detector with the bearing portion as a fulcrum can be held in a well-balanced state by the inertia mass, and the well-balanced state can be maintained by adjusting the position of the inertia mass by operation of the node alignment mechanism. Moreover, incoincidence of the center of the weight of the viscosity detector with the bearing portion can adequately be corrected by adjusting the node alignment mechanism.

The node alignment mechanism assures reliability of the viscosity detector in practical use of the latter, and moreover, makes it possible to elevate the reputation of the viscosity detector in the commercial market.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly, the above and other objects of the present invention will be apparent to those skilled in the art by referring to the summary of the invention, the detailed description of the preferred embodiment, and the claims taken in conjunction with the accompanying drawings.

DESCRIPTION OF THE PREFERRED EMBODIMENT

The present invention will now be described in detail with reference to the accompanying drawings which illustrate preferred embodiments thereof.

Figure 1:
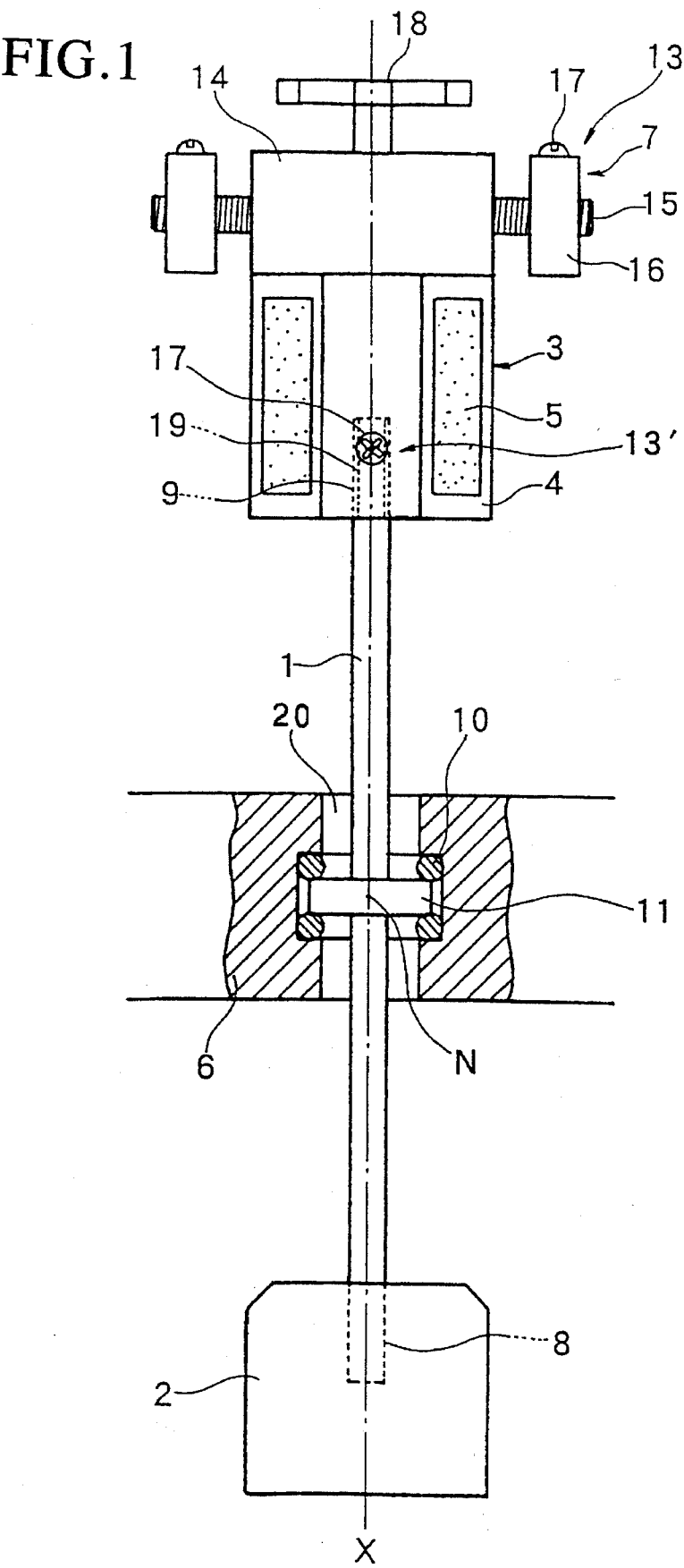
FIG. 1 is a partially exploded side view of a viscosity detector constructed in accordance with an embodiment of the present invention.

A viscosity detector is shown in FIG. 1 and includes a vibration transmission shaft 1 having a lower end which is integrated with a liquid detecting member 2. This liquid detecting member 2 is designed in the form of a column, a cylinder, a sphere, a cone or the like. The vibration transmission shaft 1 is vibrated about a central longitudinal axis X by means of a circumferential vibrator 3 which is integrated with the vibration transmission shaft 1. The circumferential vibrator 3 is a piezoelectric type vibrator which is designed such that piezoelectric plates 5, such as piezoelectric ceramic plates, are laminated on the surface of a vibrating plate 4 on one side or both sides to carry out twist vibration about an axis line. As a movement pattern, one end of the vibrator performs a circular movement or the whole vibrator performs a circular movement about the central axis. Thus, the vibration of the vibrating plate 4 assumes various types of patterns.

A bearing portion 6 is disposed at the intermediate part of the vibration transmission shaft 1. The liquid detecting member 2 is disposed on the lower end of the vibration transmission shaft 1, while an inertia mass 7 is connected at the upper end of the vibration transmission shaft 1.

The liquid detecting member 2 is a mass body and is threadedly attached to the lower end part of the vibration transmission shaft 1 so as to enable the liquid detector 2 to be displaced in the axial direction. As shown in FIG. 1, the bearing portion 6 supports the intermediate part of the vibration transmission shaft 1 which extends through the bearing portion 6. The vibration transmission shaft 1 extends from the bearing portion 6 in opposite directions. One half of the vibration transmission shaft 1 is coaxially integrated with the liquid detecting member 2, while the other half of the vibration transmission shaft 1 is integrated with the inertia mass 7. Also, the inertia mass 7 is threadedly connected to the vibrating shaft at 9 so as to enable the inertia mass 7 to be displaced along the central axis of the vibration transmission shaft 1.

The bearing portion 6 is supported possibly vibration-free relative to the vibration transmission shaft 1 by means of a pair of elastic rings 10.

Figure 2:
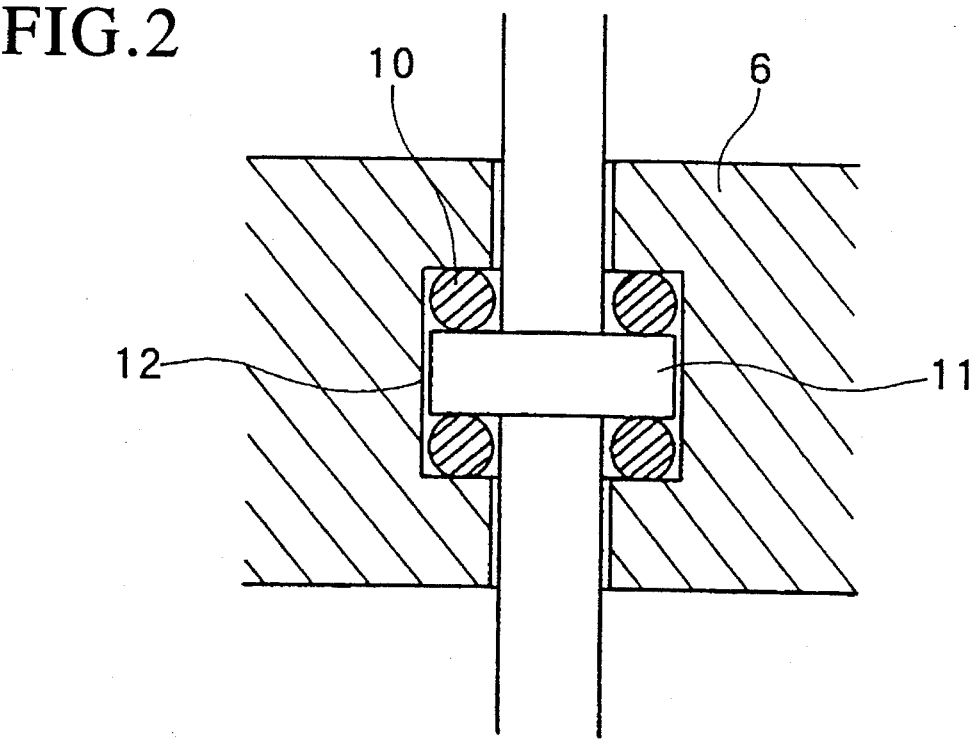
FIG. 2 is a sectional view of a bearing portion shown in FIG. 1.
Figure 3:
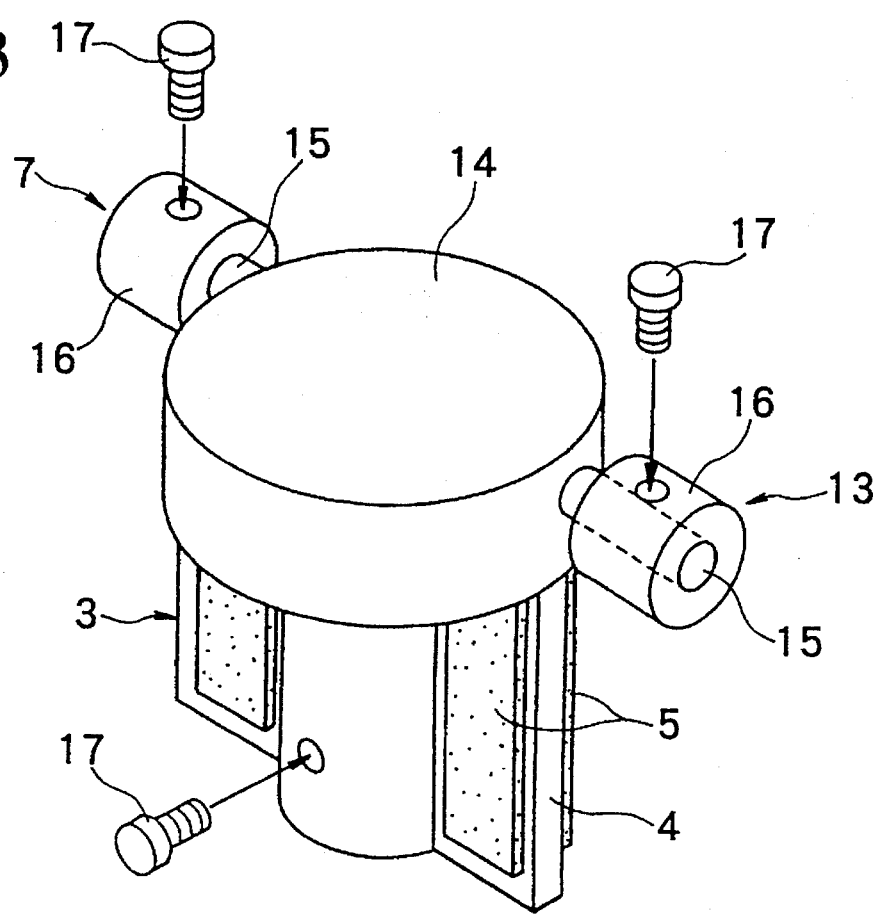
FIG. 3 is a perspective view which shows an inertia mass, a node alignment mechanism and a vibrating member of the viscosity detector shown in FIG. 1.
Figure 4:
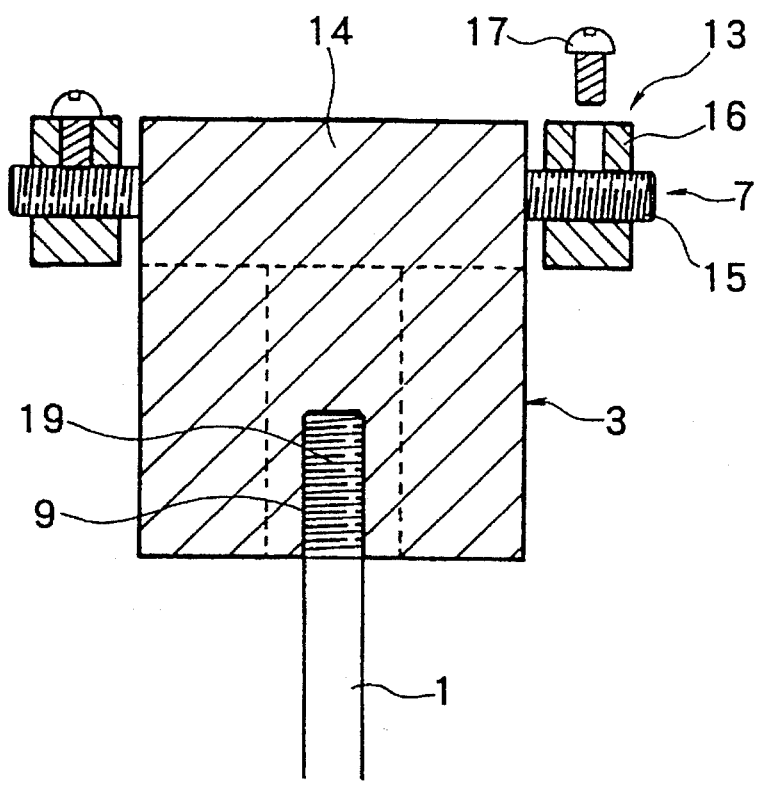
FIG. 4 is a sectional view of the inertia mass, the node alignment mechanism and the vibrating member shown in FIG. 3.
Figure 5:
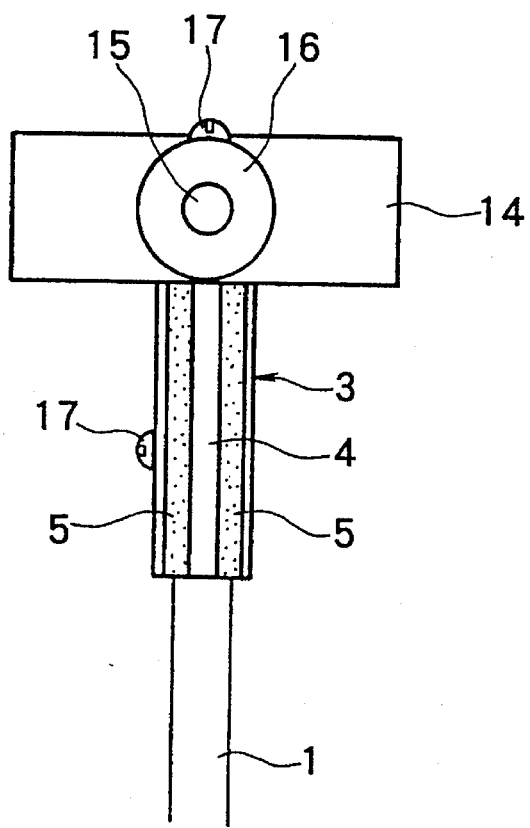
FIG. 5 is a side view of the inertia mass, the node alignment mechanism and the vibrating member shown in FIG. 3.

As shown in FIG. 1 and FIG. 2, a flange 11 is integrated with the vibration transmission shaft 1 at the intermediate part of the latter, and an elastic ring receiving groove 12 is formed in association with a through hole 20 of the bearing portion 6. A pair of elastic rings 10 is fitted onto the vibration transmission shaft 1 with the flange 11 interposed therebetween, and the elastic rings 10 are received in the receiving groove 12 together with the flange 10 so that they are held in a compressed state between the inner wall surface of the receiving groove 12 and the outer surface of the flange 11.

With such compression, the flange 11 of the vibration transmission shaft 1 is elastically connected to the bearing portion 6 via the elastic rings 10. As a result, the bearing portion 6 is connected to the vibration transmission shaft 1 in a vibration-free manner with the aid of the elastic rings 10 so that the bearing portion 6 is fitted to the vibration transmission shaft 1 at a predetermined position of the latter while preventing displacement and inclination of the bearing portion 6 in the axial direction.

The bearing portion 6 is a symmetrical circular or square supporting member adapted to support the vibration transmission shaft 1. The bearing portion 6 serves as a means for supporting the vibration transmission shaft 1 in a housing in a suspended state. In other words, the liquid detector 2 and the inertia mass 7, fitted to the opposite ends of the vibration transmission shaft 1 exclusive of the bearing portion 6, are supported in the suspended state by fixedly securing the bearing portion 6 to a housing so that the liquid detector 2 projects outside of the housing so as to be dipped in a liquid to be measured.

Otherwise, the bearing portion 6 serves as a means for supporting the whole apparatus in the suspended state by securing the apparatus to a container of liquid to be measured or to a pipe having liquid flowing therethrough.

A node alignment mechanism 13 is arranged on the inertia mass 7. The part of the inertia mass 7 is disposed so as to be displaced in the direction toward or away from a vibration transmission shaft axis X.

The direction of displacement of a portion of the inertia mass is a direction perpendicular to the vibration transmission shaft axis X. Alternatively, the inertia mass 7 may be displaced in a slantwise direction of the vibrating shaft line X. It is preferable that the inertia mass 7 is disposed so as to enable it to be equally displaced in the leftward/rightward direction relative to the vibration transmission shaft axis X.

As another example, a node alignment mechanism 13' is arranged such that the whole or a part of the inertia mass 7 is displaced along the direction of the vibration transmission shaft axis X.

The node alignment mechanism 13', for displacing the inertia mass 7 along the direction of the vibration transmission shaft axis X and the node alignment mechanism for displacing the inertia mass 7 in the direction toward or away from the vibration transmission shaft axis X, are individually used or both mechanisms are used in the integrated state.

Next, an example of the node alignment mechanism 13 for displacing the inertia mass 7 toward or away from the vibration transmission shaft axis X will be described below.

A stationary mass is fixedly disposed on the vibration transmission shaft 1 which is located at a central portion of bearing portion 6. Threaded shafts 15 extend at a right angles relative to the vibration transmission shaft 1, and movable masses 16 are threadedly fitted to the threaded shafts 15 so that they can be equally displaced toward or away from the shaft 1.

Each of the movable masses 16 includes fixing means for firmly holding the movable mass 16 at a predetermined position on the threaded shaft 15. For example, the means for firmly holding the movable mass 16 is a screw 17 which extends through the movable mass 16. By tightening the screw 17 against the threaded shaft 15, the movable mass 16 is secured in a desired position on the threaded shaft 15.

In this embodiment, the movable masses are threadedly connected to the threaded shaft 15. Alternatively, the threaded shaft may be changed to a slide shaft so that the movable masses 16 are firmly placed on the slide shaft by tightening screws 17. The threaded shaft and the slide shaft serve as a guide shaft for displacement of the movable mass 16 therealong.

Next, a node alignment mechanism 13' for permitting displacement of the inertia mass 7 along the direction of the vibration transmission shaft axis X will be described below. The vibrating member 3 is a piezoelectric device which is constructed such that a piezoelectric plate is adhesively attached to the vibrating plate 4. The vibrating plate 4 is integrally disposed on the center line of the lower end surface of the inertia mass 7. As shown in FIG. 1, the vibration transmission shaft 1 is inserted into the center of the vibrating plate 4, and the inserted shaft end is provided with a threaded shaft end 19. The threaded shaft end 19 is threadedly connected to the vibrating plate 4 and the inertia mass 7 at 9. The inertia mass 7 and the vibrating member 3 can be displaced together along the axial direction while adjusting a quantity of threaded engagement, and the threaded shaft end 19 can be firmly fixed at a predetermined displacement position by tightening a screw 17.

Figure 7:
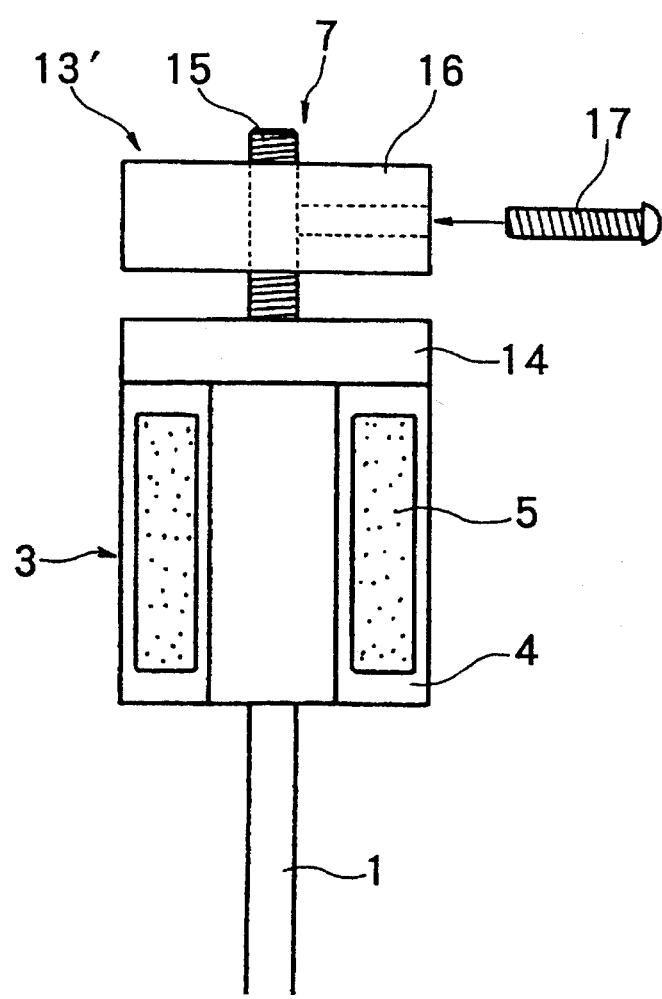
FIG. 7 is a side view of an inertia mass and node alignment mechanism constructed in accordance with another embodiment of the present invention.

In this embodiment, mass members 14 and 16 can be displaced together, i.e., the whole inertia mass can be displaced. Alternatively, as shown in FIG. 7, a part of the inertia mass 7 can be displaced in the direction of the vibration transmission shaft axis X. A threaded shaft 15 projects upwardly from a stationary mass, and a movable mass 16 is threadedly connected to the threaded shaft 15 so that the movable mass 16 can immovably be held by a tightening screw 17.

Figure 6:
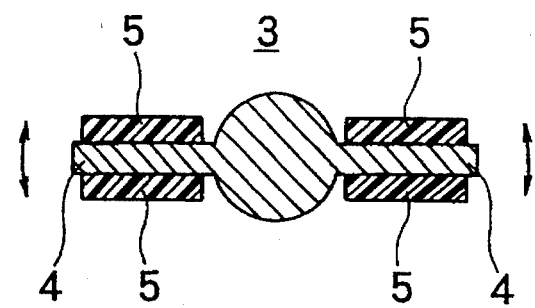
FIG. 6 is a sectional view of a piezoelectric device type vibrator.

As shown in FIG. 6, while the vibration transmission shaft 1 is located in a central location, a part of the vibrating member extending in a radial direction and another part of the vibrating member extending in an opposite radial direction circular-directionally vibrate in opposite directions to each other so that a circular directional vibrating force is imparted to the vibration transmission shaft 1.

The stationary mass 14 is formed as a single component or, due to the necessity for assembling the movable mass 7 with the guide shaft 15, it is formed from two or more components.

A vibration sensor 18 is disposed together with the vibration transmission shaft 1. When the liquid detector 2 is dipped in a liquid to be measured, the vibration sensor 18 functions as a so-called mechanical-electrical converting element which detects the variation of vibration of the vibrating member 3 to output an electrical signal, and the vibrating member 3 functions as a so-called electrical-mechanical element which is voltage-driven to produce a circular directional vibration.

The vibration sensor 18 is disposed on the vibration transmission shaft axis X on the outer end side of the inertia mass 7.

As described above, while the bearing portion 6 is disposed at the intermediate position, the liquid detector 2 is disposed at one shaft end in alignment with the vibration transmission shaft axis X, and the inertia mass 7 is disposed at the other shaft end in alignment with the vibration transmission shaft axis X. The liquid detector 2 and the inertia mass 7 are arranged in a well-balanced state from the viewpoint of vibration. By adjusting the well-balanced state, i.e, by adjusting a node N of the vibration, the position of the node N coincides with the supporting part of the bearing portion 6.

Referring to the embodiment, the node N is adjusted to be located at the center of the flange 11, which is a supporting position of the bearing portion, so that the viscosity detector is secured to a housing or the like at the bearing portion 6 in a suspended state.

According to the present invention, the vibration of the liquid detector can be balanced with the vibration of the inertia mass with the bearing portion as a fulcrum. The balanced position can exactly be determined by adjusting the position of the inertia mass with the aid of the alignment mechanism, and if the position of the node and the position of the bearing portion do not coincide, the position can easily and adequately be corrected.

In addition, the alignment mechanism can remarkably improve the reliability of the viscosity detector in construction as well as in use.

While some preferred embodiments of a viscosity detector according to the present invention have thus far been described with reference to the drawings, it should be borne in mind that such embodiments are merely illustrative of the gist of the present invention and are accordingly subject to modification and change.

What is claimed is:

1. A viscosity detector comprising:

a vibration transmission shaft having a first end, a second end, and a central longitudinal axis;

a vibration member connected to said first end of said vibration transmission shaft;

a liquid detector connected to said second end of said vibration transmission shaft;

a bearing portion disposed at an intermediate position of said vibration transmission shaft between said vibration member and said liquid detector;

an inertia mass connected to said first end of said vibration transmission shaft along the central axis thereof; and a node alignment mechanism for displacing at least a portion of said inertia mass in a direction toward or away from the central axis of said vibration transmission shaft.

2. The viscosity detector as claimed in claim 1, wherein said inertia mass is displaceable along the central axis of said vibration transmission shaft.

3. The viscosity detector as claimed in claim 1, wherein said node alignment mechanism comprises:

a first threaded shaft extending from said inertia mass in a direction which is perpendicular to said central axis; and a second threaded shaft, which is diametrically opposed to said first threaded shaft, extending from said inertia mass in a direction which is perpendicular to said central axis, wherein a first portion and a second portion of said inertia mass are threadedly mounted on said first and second threaded shafts, respectively.

4. A viscosity detector comprising:

a vibration transmission shaft having a first end, a second end, and a central longitudinal axis;

a vibration member connected to said first end of said vibration transmission shaft;

a liquid detector connected to said second end of said vibration transmission shaft;

a bearing portion disposed at an intermediate position of said vibration transmission shaft between said vibration member and said liquid detector;

an inertia mass connected to said first end of said vibration transmission shaft; and a node alignment mechanism for displacing at least a part of said inertia mass along the direction of the central axis of said vibration transmission shaft.

5. The viscosity detector as claimed in claim 4, wherein said node alignment mechanism comprises a threaded shaft extending from said inertia mass along the central axis of said vibration transmission shaft, and a portion of said inertia mass is threadedly engaged with said threaded shaft for movement along the central axis of said vibration transmission shaft.

* * * * *